(12) United States Patent
Hornegger et al.

(10) Patent No.: US 7,848,498 B2
(45) Date of Patent: Dec. 7, 2010

(54) OPERATING METHOD FOR A SUPPORT FACILITY FOR A MEDICAL ENGINEERING SYSTEM AND OBJECTS CORRESPONDING HEREWITH

(75) Inventors: Joachim Hornegger, Effeltrich (DE); Elmar Nöth, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1398 days.

(21) Appl. No.: 11/297,062

(22) Filed: Dec. 8, 2005

(65) Prior Publication Data

US 2006/0139136 A1 Jun. 29, 2006

(30) Foreign Application Priority Data

Dec. 8, 2004 (DE) .......................... 10 2004 059 166

(51) Int. Cl.
*H04M 11/00* (2006.01)
*A61B 1/04* (2006.01)
(52) U.S. Cl. .............. 379/93.25; 379/90.01; 379/93.17; 345/8
(58) Field of Classification Search .............. 379/93.25, 379/90.01, 93.01, 93.05, 93.06, 93.17, 93.19, 379/106.02, 110.01; 345/8; 600/1, 130; 700/258; 704/275, 200, 270, 230, 271, 225
See application file for complete search history.

(56) References Cited

U.S. PATENT DOCUMENTS

| 5,440,606 | A | 8/1995 | Faul et al. |
| 6,278,975 | B1 * | 8/2001 | Brant et al. .................. 704/275 |
| 7,310,072 | B2 * | 12/2007 | Ronzani et al. ................ 345/8 |
| 7,395,249 | B2 * | 7/2008 | Wang et al. ................... 706/14 |
| 2002/0101568 | A1 | 8/2002 | Eberl et al. |
| 2002/0105482 | A1 | 8/2002 | Lemelson et al. |
| 2004/0106916 | A1 * | 6/2004 | Quaid et al. ................... 606/1 |
| 2006/0200354 | A1 * | 9/2006 | Ito et al. ..................... 704/275 |

FOREIGN PATENT DOCUMENTS

| DE | 200 01 134 U1 | 6/2000 |
| DE | 100 61 782 A1 | 6/2002 |
| DE | 101 03 922 A1 | 8/2002 |
| EP | 0 353 459 A1 | 2/1990 |
| WO | WO 98/31280 A1 | 7/1998 |
| WO | WO 02/100285 A1 | 12/2002 |

* cited by examiner

Primary Examiner—Melur Ramakrishnaiah

(57) ABSTRACT

An inquirer provides a support facility for a medical engineering system with a voice entry by means of a voice entry device. The support facility evaluates the voice entry by means of a voice recognition system and reacts correspondingly in that it outputs an acoustic output to the inquirer via an acoustic output device and an optical output via an optical device.

14 Claims, 2 Drawing Sheets

OPERATING METHOD FOR A SUPPORT FACILITY FOR A MEDICAL ENGINEERING SYSTEM AND OBJECTS CORRESPONDING HEREWITH

CROSS REFERENCE TO RELATED APPLICATION

This application claims priority of the German application No. 10 2004 059 166.0 DE filed Dec. 8, 2004, which is incorporated by reference herein in its entirety.

FIELD OF THE INVENTION

The present invention relates to an operating method for a support facility for a medical engineering system, with an inquirer of the support facility providing a voice entry and the support facility evaluating the voice entry by means of a voice recognition system and reacting correspondingly to the evaluated voice entry.

BACKGROUND OF THE INVENTION

The present invention further relates to a data carrier with a computer program stored on the data carrier for programming such a support facility, so that the support facility implements an operating method of the type mentioned above when the computer program is called. Furthermore the present invention relates to a corresponding support facility and a medical engineering system with such a support facility.

Medical engineering systems are generally known. Examples of systems of this type are computer tomographs, ultrasound tomographs, magnetic resonance tomographs, angiography systems etc. In particular, the above-mentioned complex medical engineering systems are often equipped with so many functions and options that a very extensive operating user interface and a very extensive functionality are thus available. The implementation of less frequently required examination sequences is thus only possible in practice using a user handbook.

Naturally, the user of the medical engineering system is in principle able to acquire the corresponding knowledge and subsequently, with or without the user handbook, implement the rather infrequently used examination sequence. In practice, the user often shies away from the outlay in cost and time related to reading up and familiarizing him/herself with said examination sequence. The medical engineering system is consequentially only used to a limited extent. A part of its potential is lost, as it were, even before it starts.

A basically identical problem arises during inspection, maintenance and repair work, if work other than routine tasks is to be carried out. In this case, it is however imperative that the maintenance personnel familiarize themselves with the handbook and/or with the service instructions.

The prior art attempts to avoid the problem outlined above by replacing and supplementing the printed operating instructions and/or user handbooks etc. by digital operating instructions and user handbooks. These electronic documents can then be viewed using a computer, for instance by means of a web browser. In this case, the computer can be a component of the medical engineering system.

However in a large number of cases, this suggestion also only results in unsatisfactory results, since the familiarization must be carried out by those who require the corresponding knowledge. The time and cost expenditure involved in reading up and familiarizing oneself thus remains unchanged. Only the medium, by means of which the information required for familiarization is made available, has been changed.

In recent times simulation systems have also become known, by means of which it is possible to familiarize oneself with the medical engineering system and its functionalities. The familiarization here also requires enormous cost and time outlay. Furthermore, in this case, the person who wishes to acquire the required knowledge is restricted in his/her local maneuverability, since the required knowledge is only made available to him/her at a computer output unit (a screen or the like).

If the person, for whatever reason, wishes to carry out tasks at a location at or with the medical engineering system, from which the computer output unit is not visible, the above-mentioned simulation systems are also unsuitable and are not accepted in practice.

There is thus the need for a solution which allows a person to use the complete potential of a medical engineering system, if, on the one hand they are not familiar with all the functionalities of the medical engineering system and on the other hand it is not known where the user will be located at the medical engineering system.

SUMMARY OF THE INVENTION

The object is achieved according to the claims by an operating method for a support facility of the type mentioned at the beginning, in which the support facility outputs both an acoustic and also an optical output to the inquirer in reaction to the voice entry.

The object is thus correspondingly achieved by a support facility with the features of the claims.

The advantages of the present invention are particularly effective if the support facility guides the inquirer step-by-step through a treatment process to be implemented with or at the medical engineering system, and the support facility awaits a response from the inquirer prior to the next reaction in each instance.

If the optical output takes place by projecting visual information onto a partially transparent visor of a visualization device to be attached to the head of an inquirer, the inquirer can then also be provided with an optical output even if they move around within the medical engineering system for instance.

If the position and orientation of the visualization device in the room are detected by means of a sensor technology, and the projected visual information is adapted to the position and orientation of the visualization device in the room, the operating method operates even better. In particular, it is possible in this case to project visual information such that it appears to be available to the observer at a location in the room to which the information relates. By way of example, a marker (e.g. an arrow) can be projected such that it points to an element of the medical engineering system at or with which the enquirer is to carry out his/her next treatment. For instance, during the treatment of a patient, an examination result of a previously implemented examination can be projected in a locationally correct manner.

If the projected visual information is correspondingly updated during a change in the position and orientation of the visualization device in the room, the operating method operates even better. In this case, the visual information can be updated such that it appears to be independent of the movement of the visualization device in the room.

The sensor technology for detecting the position and orientation of the visualization device in the room can be separated from the visualization device. It is however preferably connected to the visualization device.

If the voice entry takes place by means of a voice entry device to be attached to the head of the inquirer, voice entries are possible in a particularly reliable manner and in particular with a good signal-to-noise ratio. In this case, the voice entry device can be integrated with the visualization device into a joint head unit. In principle, another embodiment of the voice entry device would also be possible, e.g. as a microphone array, preferably arranged in a fixed manner.

As previously mentioned, the acoustic and the optical output can be information about the medical engineering system as such or about a patient to be treated by means of the medical engineering system. Other outputs are also conceivable.

If, in reaction to the voice entry, the support facility also influences the operating state of the medical engineering system, the operating method according to the invention operates even better. In particular, complete control of the medical engineering system can be possible without an inquirer needing their hands. The inquirer can thus implement other tasks with their hands, for example treating a patient or repairing the medical engineering system.

BRIEF DESCRIPTION OF THE DRAWINGS

Further advantages and details are set down in the description below of an exemplary embodiment in conjunction with the drawings, in which.

DETAILED DESCRIPTION OF THE INVENTION

Figure 1:
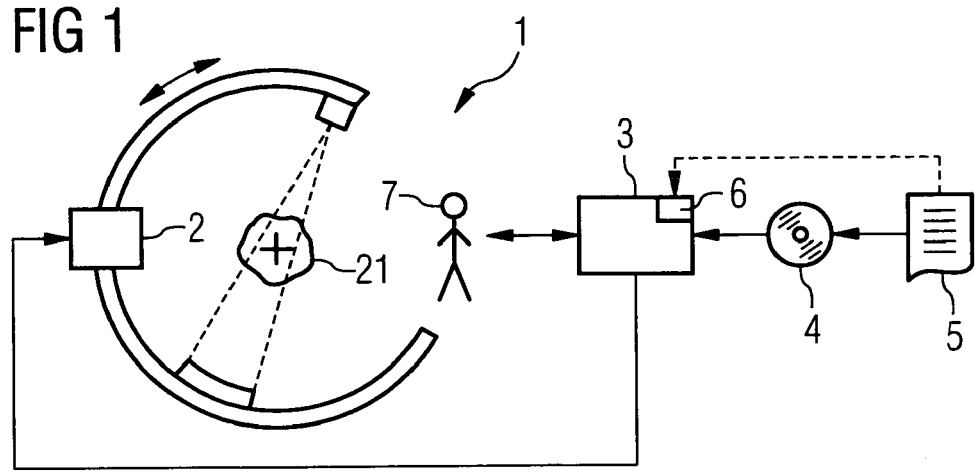
FIG. 1 shows a schematic diagram of a medical engineering system and a support facility

According to FIG. 1 a medical engineering system 1 is designed as a C-arm angiography system. This embodiment is however strictly exemplary. Alternatively the medical engineering system 1 could also be designed for example as a computer tomograph, an ultrasound tomograph, or as a magnetic resonance system etc. Other embodiments are also possible.

The medical engineering system 1 of FIG. 1 can also be controlled by means of a control device 2. The control device 2 is connected to a support facility 3 for the medical engineering system.

A computer program 5 is stored on a data carrier 4 in an (exclusively) machine-readable form. The computer program 5 serves to program the support facility 3. The support facility 3 is stored in a memory 6. The support facility 3 implements an operating method when the computer program is called, said operating method being described below in greater detail in conjunction with FIG. 4.

Figure 2:
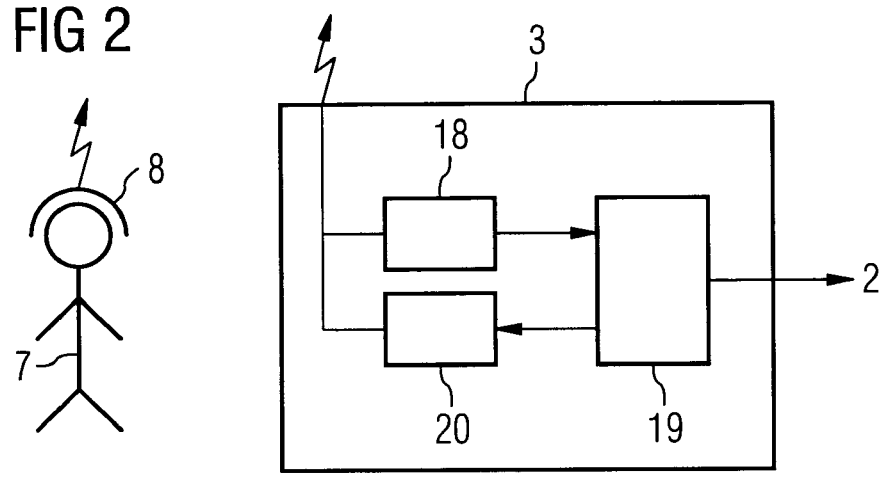
FIG. 2 shows a schematic diagram of an inquirer and the support facility in FIG. 1.

A user 7 and/or inquirer 7, these two terms are subsequently used synonymously, communicate according to FIG. 1 with the support facility 3. In this case, see FIG. 2, the communication takes place wirelessly, for instance by radio, via a head unit 8. For this purpose, besides an antenna 9, the head unit 8, see FIG. 3, comprises a voice entry device 10, an acoustic output device 11, an optical output device 12 and sensors 13 of a sensor technology. A head control device 14 is provided to control and coordinate these units 9 to 13.

Figure 3:
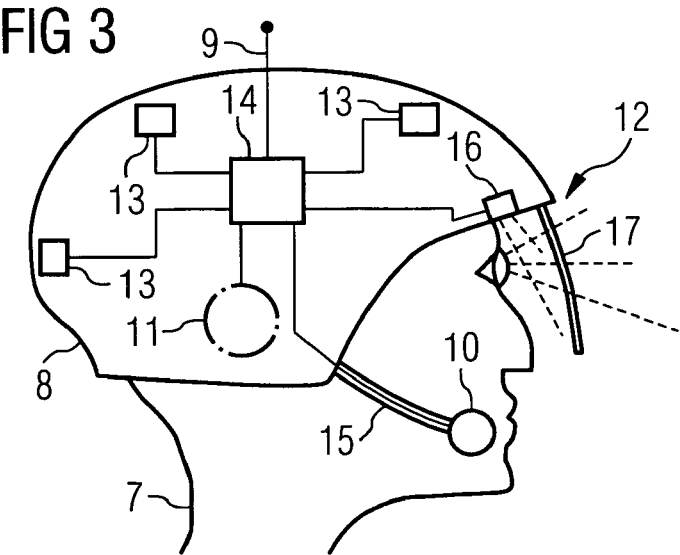
FIG. 3 shows a schematic diagram of the head of the inquirer and a head unit.

The head unit 8 is, as FIG. 3 shows, designed as a helmet 8, which can be placed on the head of the inquirer 7 and can thus be attached to the head of the inquirer 7. The head control unit 14 is integrated into the helmet 8. It is generally designed as a microprocessor 14. The voice entry device 10 is designed as a conventional microphone which is arranged near to the mouth of the inquirer 7 by means of a flexible arm 15. The acoustic output device 11 is designed as a conventional small helmet loudspeaker 12. The optical output device 12 comprises a controllable light source 16 and a partially transparent visor 17. The controllable light source 16 can be controlled by the head control unit 14 such that the optical outputs can be projected onto the visor 17. The position and the orientation of the head unit 8 (and thus implicitly also the optical output device 12, subsequently also referred to as the visualization device 12) can be detected by means of the sensors 13.

Head units 8, as they are described above, with the exception of wireless communication, are known in the prior art. By way of example, they are used as helmets for the pilots of fighter jets.

Figure 4:
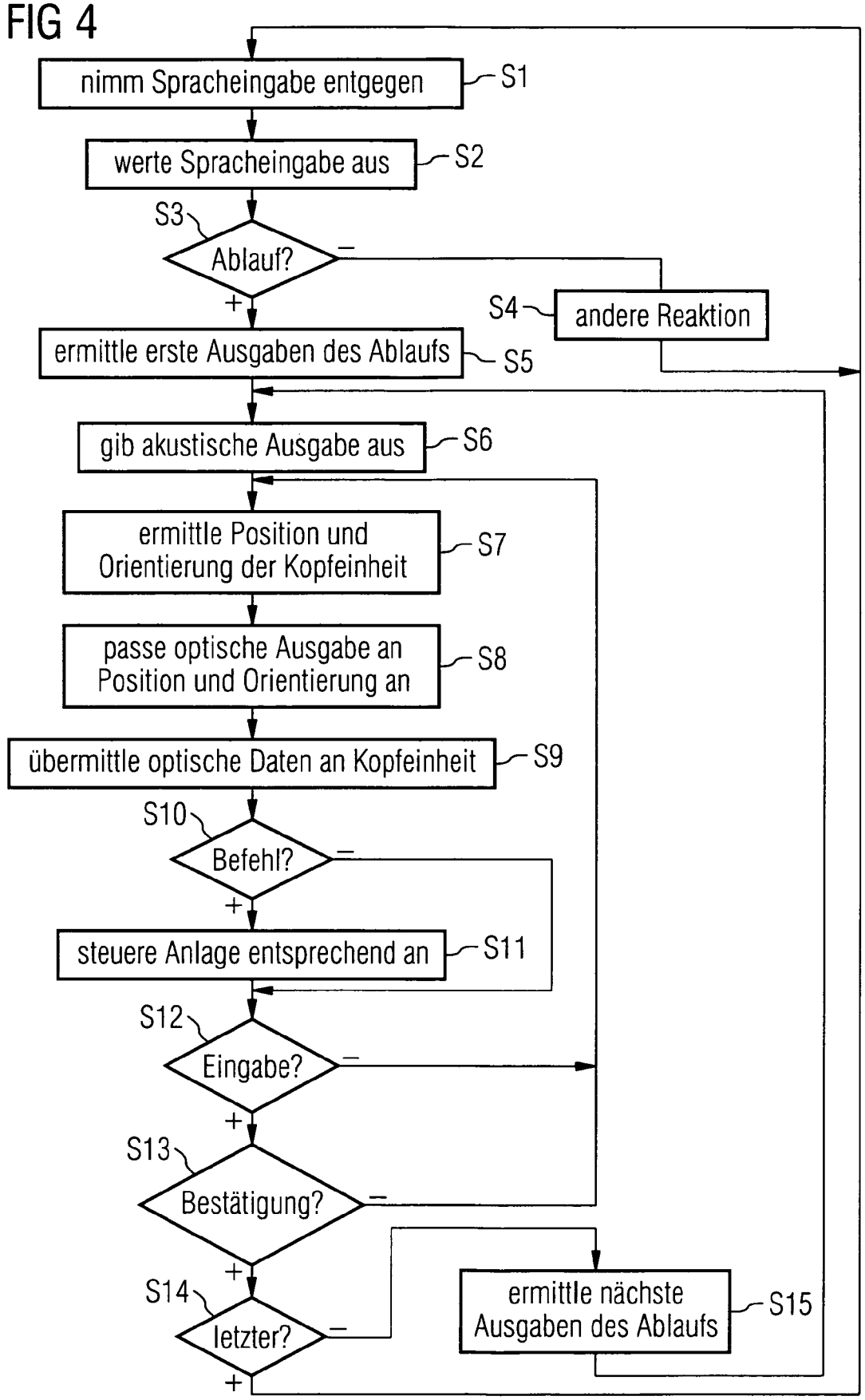
FIG. 4 shows a schematic diagram of a flowchart

The support facility 3 according to the invention operates according to FIG. 4 as follows;

The inquirer 7 first provides a voice entry via the voice entry device 10. The voice entry is accepted by the head control unit 14 and forwarded to the support facility 3 which accepts said voice entry in a step S1 via a receive device 18. The accepted voice entry is routed to a voice recognition system 19 which evaluates the voice entry in a step S2 corresponding to the voice entry provided by the inquirer 7 and reacts correspondingly thereto.

Voice recognition systems such as the voice recognition system 19 of the present invention are likewise already known. In this case, complex voice recognition systems are even able to recognize and understand a free speech of the inquirer 7. If a more simple voice recognition system 19 is used, the inquirer 7 can be requested to use predefined key terms in each instance. During each acoustic output, the inquirer can be told for instance which voice entries are permissible, possible and/or meaningful as the next entry.

In step S3 the support facility 3 examines whether a treatment process is activated by means of the voice entry. If this is not the case, a reaction takes place in step S4 which is less significant in the scope of the present invention and is thus not explained in further detail. If, in contrast, a treatment process is provided, the support facility 3 first determines, in a step S5, the first outputs of the process. In this case it is possible, in reaction to the voice entry of the inquirer 7, for both an acoustic and an optical output to be output to the inquirer 7 by means of the support facility.

The acoustic output to be output immediately transmits the support facility 3 via a transmit device 20 to the head unit 8, where it is output to the inquirer 7 via the acoustic output facility 11. Then the support facility 3 detects the position and orientation of the head unit 8 in the room, by means of the sensors 13 in the sensor technology. The position and orientation of the visualization device 12 are thus implicitly also given. In a step S8 the support facility 3 then adapts the optical output to be output to the position and the orientation of the visualization device 12 in the room. This adapted optical output transmits the support facility 3 in a step S9 to the head unit 8. The optical output is routed to the controllable light source 16, by means of which the optical output is projected onto the visor 17.

In a step S10 the monitoring device 3 checks whether, due to the treatment process to be carried out, a control command is to be transmitted to the control device 2 of the medical engineering system 1. If this is the case, the control command is transmitted to the control device 2 and thus correspondingly controls the medical engineering system, thus influencing the operating state thereof.

The control device 3 next examines, in a step S12, whether the inquirer 7 has made a new voice entry. If they have not, the process returns to step S7. Since in step S7 the position and orientation of the head unit 8 is now detected (again), and the steps S8 and S9 are subsequently executed again, the information projected onto the visor 17 is correspondingly updated during a change in the position or orientation of the visualization device 12 in the room.

If there is a voice entry, the monitoring device 3 checks, in a step S13, whether the voice entry is a confirmation of the inquirer 7. It thus checks whether a response has arrived from the inquirer 7. If this is not the case, in the process continues at step S7. Alternatively, if a confirmation was provided, the monitoring device 3 checks, in a step S14, whether the last step of the treatment process to be implemented has already been implemented. If this is not the case, the support facility determines, in a step S15, the next outputs of the process and thus returns to step S6 or alternatively to step S1.

As a result of the execution sequence described above, the support facility thus guides the inquirer 7 step-by-step through the treatment process. The support facility 3 awaits a response from the inquirer 7, prior to the next reaction in each instance.

The treatment process can alternatively be implemented with the medical engineering system 1 or at the medical engineering system 1.

By way of example, a patient 21 can be examined or treated. In this case the support facility 3 provides the inquirer 7 with consecutive acoustic outputs which contain treatment instructions. At the same time, information is also projected onto the visor 17, at least for some of the outputs. By way of example, it is possible to indicate where a doctor should make a cut or where a catheter is currently located. A vessel structure of the patient 21 can also be shown at the correct location.

If a treatment process is to be carried out at the medical engineering system 1, the treatments to be carried out are provided acoustically consecutively to the inquirer 7. A marker is simultaneously shown, so that the element of the medical engineering system 1, at which the inquirer 7 is to carry out the respective treatment step, is marked.

The inventive procedure thus replaces a printed or electronic user handbook by means of a dialog with an intelligent, automatic voice recognition system 19, which gradually guides the inquirer 7 through the necessary steps of a treatment process.

In this case, the so-called augmented reality is preferably used to point to components of the medical engineering system 1, in which corresponding markers are projected onto the visor 17. The inquirer 7 can thus also implement difficult operating sequences which are normally only possible after extensively studying a user handbook. Furthermore, all entries and outputs take place acoustically and optically. The inquirer 7 thus has his hands free for all treatments.

The invention claimed is:

1. An operating method for a support facility for a medical engineering system, comprising:
    providing a voice entry by an inquirer of the support facility;
    evaluating the voice entry by a voice recognition system by the support facility; and
    reacting according to the evaluated voice entry by the support facility,
    wherein the support facility outputs both an acoustic and an optical output to the inquirer in reaction to the voice entry,
    wherein the optical output takes place by projecting a visual information onto a partially transparent visor of a visualization device to be attached to the head of the inquirer, and
    wherein the position and orientation of the visualization device in the room is detected by a sensor technology and that the projected visual information is adapted to the position and orientation of the visualization device in the room.

2. The operating method according to claim 1, wherein the support facility guides the inquirer step-by-step through a treatment process to be carried out with or at the medical engineering system and that the support facility awaits a response from the inquirer before the respective next reaction.

3. The operating method according to claim 1, wherein the projected visual information is correspondingly updated during a change in position and orientation of the visualization device in the room.

4. The operating method according to claim 1, wherein the voice entry takes place by a voice entry device to be attached to the head of the inquirer.

5. The operating method according to claim 1, wherein the acoustic and optical outputs provide information towards an operation of the medical engineering system or a maintenance procedure regarding the medical engineering system.

6. The operating method according to claim 1, wherein the acoustic and the optical output are information about a patient to be treated by the medical engineering system.

7. The operating method according to claim 1, wherein the support facility also influences the operating state of the medical engineering system in reaction to the voice entry.

8. A support facility for a medical engineering system, comprising:
    a voice entry device that provides a voice entry from an inquirer;
    a voice recognition system that evaluates the voice entry; and
    an acoustic and an optical output device such that an acoustic and an optical output can be output to the inquirer by the support facility in reaction to the voice entry,
    wherein the optical output device is designed as a visualization device to be attached to the head of the inquirer, and the visualization device comprises a partially transparent visor onto which the optical output can be projected, and
    wherein the support facility comprises a sensor technology such that the position and orientation of the visualization device in the room can be detected, and is designed such that it adapts the projected visual information to the position and orientation of the visualization device in the room.

9. The support facility according to claim 8, wherein the support facility is designed such that it guides the inquirer step-by-step through a treatment process to be implemented with the medical engineering system or at the medical engineering system and awaits a response from the inquirer prior to the next reaction in each instance.

10. The support facility according to claim 8, wherein the support facility is designed such that it correspondingly updates the projected visual information during a change in position and/or orientation of the visualization device in the room.

11. The support facility according to claim 8, wherein the sensor technology is connected to the visualization device.

12. The support facility according to claim 8, wherein the voice entry device is attached the head of the inquirer.

13. The support facility according to claim 11, wherein the voice entry device is attached the head of the inquirer and the visualization device and the voice entry device are integrated in a common head unit.

14. The support facility according to claim 8, wherein the support facility is connected to a control device for the medical engineering system and is designed such that in reaction to the voice entry, said medical engineering system can output the control commands influencing the operating state of the medical engineering system to the control device.

* * * * *